United States Patent [19]
Lehn et al.

[11] Patent Number: 5,457,184
[45] Date of Patent: Oct. 10, 1995

[54] RARE EARTH MACROCYCLIC COMPLEXES AND USE THEREOF FOR REDUCTION OF DISTURBANCES IN AN ASSAY USING FLUORESCENCE

[75] Inventors: Jean-Marie Lehn; Christine O. Roth, both of Strasbourg; Gérard Mathis, Bagnols Sur Ceze, all of France

[73] Assignee: Cis Bio International, Saclay, France

[21] Appl. No.: 199,135

[22] PCT Filed: Aug. 28, 1992

[86] PCT No.: PCT/FR92/00832

§ 371 Date: Feb. 25, 1994

§ 102(e) Date: Feb. 25, 1994

[87] PCT Pub. No.: WO93/05049

PCT Pub. Date: Mar. 18, 1993

[30] Foreign Application Priority Data

Aug. 30, 1991 [FR] France ................. 91 10809

[51] Int. Cl.⁶ .......... C07F 5/00; C07D 245/00; C07D 225/00
[52] U.S. Cl. .......... 534/15; 534/16; 540/460; 540/465; 540/470
[58] Field of Search .............. 540/456, 460, 540/465, 470, 474; 546/296; 534/15, 16

[56] References Cited

U.S. PATENT DOCUMENTS

| | | | |
|---|---|---|---|
| 4,761,481 | 8/1988 | Hale et al. ............... | 546/296 |
| 4,927,923 | 5/1990 | Mathis et al. ............ | 540/456 |
| 5,220,012 | 6/1993 | Mathis et al. ............ | 540/459 |
| 5,403,928 | 4/1995 | Arrhennis ................ | 540/128 |

FOREIGN PATENT DOCUMENTS 8908263  9/1989  WIPO.

OTHER PUBLICATIONS

Helvetica Chimica Acta; vol. 74. No. 3. pp. 572–578, 1991.
Helvitica Chimica Acta; vol. 73. No. 1; pp. 106–111. 1990.
Helvitica Chimica Acta; vol. 73. No. 5. pp. 1149–1162, 1990.

*Primary Examiner*—Shean Wu
*Attorney, Agent, or Firm*—Marshall & Melhorn

[57] ABSTRACT

The invention relates to macrocyclic rare earth complexes which consist of at least one rare earth salt complexed by a macrocyclic compound of formula (I):

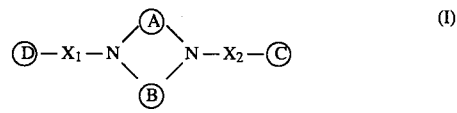

in which:
the bivalent radicals Ⓐ, Ⓑ, Ⓒ and Ⓓ, which are identical or different, are hydrocarbon chains optionally containing one or more heteroatoms, at least one of said radicals containing at least one molecular unit or essentially consisting of a molecular unit possessing a triplet energy greater than the energy of the emission level of the complexed rare earth ion, at least one of said radicals consisting of a substituted or unsubstituted nitrogen-containing heterocyclic system in which at least one of the nitrogen atoms carries an oxy group, and it being possible for one of the radicals Ⓒ or Ⓓ not to exist; and $X_1$ and $X_2$, which are identical or different, are hydrogen or a hydrocarbon chain $(CH_2)_n$ optionally interrupted by 1 or more heteroatoms, n being an integer from 1 to 10, with the proviso that if the radicals Ⓐ and/or Ⓑ are a nitrogen-containing heterocyclic system in which at least one of the nitrogen atoms carries an oxy group, the radicals Ⓒ and/or Ⓓ are selected from biquinolines, biisoquinolines, bipyridines, terpyridines, coumarins, bipyrazines, bipyrimidines and pyridines, and to their use for reducing the perturbations in a fluorescent assay.

25 Claims, No Drawings

RARE EARTH MACROCYCLIC COMPLEXES AND USE THEREOF FOR REDUCTION OF DISTURBANCES IN AN ASSAY USING FLUORESCENCE

BACKGROUND OF THE INVENTION

1. Field of the Invention

The invention relates to macrocyclic rare earth complexes, to a method of reducing perturbations in a fluorescent assay using these complexes, and to their use for reducing the perturbations in the measuring medium of a fluorescent method of detecting and/or determining an analyte in a medium in which it may be present.

2. Description of the Prior Art

Immunoassays are widely used at the present time for the qualitative and quantitative analysis of compounds in biological fluids.

Among the techniques which exist, fluorimetric assays have become increasingly important.

In fact, they have a number of advantages, including the sensitivity and rapidity of the measurement, the stability and safety of the reagents labeled with fluorescent compounds, and the relatively low cost.

It is known that methods of detection which use fluorescence are intrinsically very sensitive and might permit lower detection limits than those achieved by immunoassays which use radiolabeled reagents, in particular when using modulatable laser light sources (I. Wieder, Immunofluorescence and related staining techniques, 1978, Elsevier).

A large number of fluorescent molecules which can be used as tracers in assays of this type have been described previously and include rare earth complexes possessing valuable properties.

The use of particular complexes, namely rare earth cryptates, is described in the patent applications EP 0 180 492, PCT/FR86/00269, EP 0 321 353 or These rare earth cryptates have the advantage of being very stable in a saline protein medium, this property being particularly important in the case of homogeneous immunoassays.

The sensitivity of the measurement can nevertheless be greatly affected by difference types of perturbation resulting from the presence of various molecules in the measuring medium.

This problem is particularly acute in the case of assays in a serum medium in which numerous molecules are capable of interfering.

For example, the measured signal can be perturbed by the emission of molecules capable of being excited and of emitting at the same wavelengths as the molecule used as the tracer.

The time-resolved methods of measuring fluorescence enable this disadvantage to be partially overcome. The principle of these methods consists in measuring the fluorescence emitted by a tracer molecule having a relatively long emission lifetime, the measurement being delayed in time beyond the emission lifetime of the other molecules present.

In this case it is necessary to use fluorescent tracer molecules with a relatively long lifetime, such as rare earth chelates.

The sensitivity of the measurement can also be affected by interference from molecules in the medium capable of perturbing the variation in fluorescence resulting from the bonding between the analyte to be detected and the labeled biospecific reagent. The patent application EP 0 324 323 describes the use of a modulator which stabilizes the rare earth chelate bonded to the biospecific reagent, so that the measured fluorescence is a true function of the concentration of the analyte. The effect of this modulator is to prevent perturbation of the fluorescence of the rare earth chelate by the other molecules present in the medium. The measured variation in fluorescence is then a function of the antigen-antibody reaction only. The proposed modulators are macromolecules such as proteins and detergents, and have to be used in excess in the range from 0.1 to 10 g/l.

Nevertheless, none of these methods completely solves the problem of the perturbations due to the molecules present in the measuring medium. In fact, an important source limiting the sensitivity of the fluorescent measurement is the existence of quenching processes due to molecules present in the medium which are capable of inhibiting the fluorescence of the fluorescent molecule used as the marker in the assay. In the case of rare earth complexes, these processes can result from proximity electron transfer mechanisms, in which the inhibitor molecule occupies the coordination sites remaining free within the complex. Particular mention may be made of the redox reactions occurring between the fluorescent molecule, in its ground state or in its excited state, and molecules present in the medium. These mechanisms are capable of causing a considerable variation in the emitted fluorescence.

The article by Weber et al., Clin. Chem., 1983, 29/9, 1665–1672, describes the influence of perturbations due in particular to uric acid in the amperometric detection of a tris(2,2'-bipyridine)ruthenium(III) complex. This complex is produced by the redox reaction of the corresponding Ru(II) complex, which is capable of oxidizing a Co(III) quenching complex. Uric acid has been identified as a reducing agent for Ru(III) and is therefore capable of interfering in the measurement.

This redox mechanism, due to an electron transfer between a fluorescent compound and a quenching compound, has also been demonstrated by Sabbatini et al., J.A.C.S., 1984, 106, 4055–4056. This article describes in particular the oxidation of a complex $M(CN)_6^{4-}$, in which M is iron, ruthenium or osmium, by a europium cryptate.

The inhibition of fluorescence by mechanisms involving an electron transfer, and by quenching mechanisms in general, is an extremely troublesome phenomenon in practice because the inhibiting factors can either be naturally present as components in the measuring medium (for example uric acid in serum) or else be added thereto as additives or stabilizers for the assay.

These inhibitors greatly affect the fluorescence of the marker molecule. In particular, in the case of redox perturbing reactions, the conversion of a rare earth ion from the reduced state to the oxidized state via a redox mechanism results in a decrease in the lifetime and a modification of the emission spectrum of the complex in which it is present, thereby greatly affecting the sensitivity of the measurement.

The use of ligands of the macrocyclic type for chelating rare earth ions has been described in the literature, especially in the following publications: J. Phys. Chem., 1987, 91, 4681–4685, Inorg. Chem., 1983, 22, 3866–3869, Inorg. Chem. Acta, 1984, 95, 119–125, Nucl. Med. Biol., 1986, 13, 311–318, and Comprehensive Coordination Chemistry, 1987, vol. 3, published by Pergamon Press, and in the publication Helvetica Chimica Acta, 1990, 73, 1149–1162.

Although some of the compounds described have a low dissociation rate in water, the criterion of stability in pure water is not sufficient since serum actually contains numerous ions and proteins, some of them at high concentration, which can compete with the ligand for complexation of the rare earth ion.

SUMMARY OF THE INVENTION

Unexpectedly, it has now been found that macrocyclic rare earth complexes consisting of at least one rare earth salt complexed by a macrocyclic compound comprising at least one molecular unit possessing a triplet energy greater than the energy of the emission level of the complexed rare earth ion, and at least one nitrogen-containing heterocyclic system in which at least one of the nitrogen atoms carries an oxy group, have the advantageous property of being significantly less sensitive to the quenching of fluorescence due to the inhibitors present in the measuring medium than the known chelates and macropolycyclic and macrocyclic complexes, and of being more stable in biological media than the other known macrocyclic complexes and chelates.

They are thus particularly suitable for use as tracers in a fluorimetric assay.

DESCRIPTION OF THE PREFERRED EMBODIMENT

According to a first feature, the invention therefore relates to macrocyclic rare earth complexes which consist of at least one rare earth salt complexed by a macrocyclic compound of formula (I):

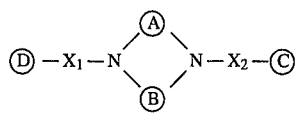

in which:
the bivalent radicals Ⓐ, Ⓑ, Ⓒ and Ⓓ, which are identical or different, are hydrocarbon chains optionally containing one or more heteroatoms, at least one of said radicals containing at least one molecular unit or essentially consisting of a molecular unit possessing a triplet energy greater than the energy of the emission level of the complexed rare earth ion, at least one of said radicals consisting of a substituted or unsubstituted nitrogen-containing heterocyclic system in which at least one of the nitrogen atoms carries an oxy group, and it being possible for one of the radicals Ⓒ and Ⓓ not to exist; ad $X_1$ and $X_2$, which are identical or different, are either hydrogen, in which case one or both radicals Ⓒ and Ⓓ do not exist, or a hydrocarbon chain $(CH_2)_n$ optionally interrupted by one or more heteroatoms, n being an integer from 1 to 10, with the proviso that if the radicals Ⓐ and/or Ⓑ are a nitrogen-containing heterocyclic system in which at least one of the nitrogen atoms carries an oxy group, the radicals Ⓒ and/or Ⓓ are selected from biquinolines, biisoquinolines, bipyridines, terpyridines, coumarins, bipyrazines, bipyrimidines and pyridines.

According to a preferred feature, the macrocyclic rare earth complexes according to the invention consist of at least one rare earth salt complexed by a macrocyclic compound of formula (I) above in which at least one of the bivalent radicals Ⓐ and Ⓑ contains at least one molecular unit or essentially consists of a molecular unit possessing a triplet energy greater than the energy of the emission level of the complexed rare earth ion, and at least one of the radicals Ⓒ and Ⓓ consists of a nitrogen-containing heterocyclic system in which at least one of the nitrogen atoms carries an oxy group.

Other advantageous macrocyclic rare earth complexes are those in which at least one of the following conditions is satisfied:
the bivalent radicals Ⓐ and Ⓑ are identical;
the bivalent radicals Ⓒ and Ⓓ are identical; and
$X_1$ and $X_2$ are identical,
with the proviso that if the radicals Ⓐ and/or Ⓑ are a nitrogen heterocyclic system in which at least one of the nitrogen atoms carries an oxy group, the radicals Ⓒ and/or Ⓓ are selected from biquinolines, biisoquinolines, bipyridines, terpyridines, coumarins, bipyrazines, bipyrimidines and pyridines.

The triplet energy-donating molecular units which are suitable for the purposes of the invention must possess a triplet energy greater than or equal to the energy of the emission levels of the rare earth ion. According to a preferred feature, the triplet level of said molecular unit is greater than 17,300 cm$^{-1}$.

Molecular units which are particularly preferred for the purposes of the invention are phenanthroline, anthracene, bipyridines and biquinolines, especially bisisoquinolines, for example 2,2'-bipyridine, terpyridines, coumarins, bipyrazines, bipyrimidines, azobenzene, azopyridine, pyridines or 2,2'-bisisoquinoline, or the units

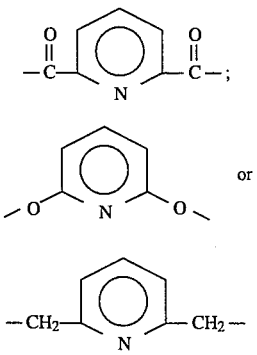

According to an advantageous feature, the nitrogen-containing heterocyclic system in which at least one of the nitrogen atoms carries an oxy group is selected from the following units: pyridine N-oxide, bipyridine N-oxide, bipyridine di-N-oxide, bisisoquinoline line N-oxide, bisisoquinoline di-N-oxide, bipyrazine N-oxide, bipyrazine di-N-oxide, bipyrimidine N-oxide and bipyrimidine di-N-oxide.

Other preferred macrocyclic complexes are those in which the molecular unit possessing a triplet energy greater than the energy of the emission level of the complexed rare earth ion, and the nitrogen heterocyclic system in which at least one of the nitrogen atoms carries an oxy group, are one and the same unit.

Rare earth ions which can be used in particular in the complexes of the invention are terbium, europium, samarium and dysprosium ions. Terbium or europium will preferably be used.

The macrocyclic complexes are particularly suitable as fluorescent markers for biological substances.

For this purpose, the complexes according to the invention can be substituted on at least one of the compound by a group Ⓐ, Ⓑ, Ⓒ and Ⓓ of the macrocyclic compound by a group —CO—NH—Y—Z, which:

Y is a spacer arm or group which consists of a bivalent organic radical selected from linear or branched $C_1$ to $C_{20}$ alkylene groups optionally containing one or more double bonds and/or optionally interrupted by one or more heteroatoms such as oxygen, nitrogen, sulfur or phosphorus, from $C_5$–$C_8$ cycloalkylene groups or from $C_6$ to $C_{14}$ arylene groups, said alkylene, cycloalkylene or arylene groups optionally being substituted by alkyl, aryl or sulfonate groups; and Z is a functional group capable of bonding covalently with a biological substance.

In the present description, "functional group capable of bonding covalently with a biological substance" is understood as meaning any functional group which is capable of bonding covalently, directly or after activation, with at least one of the functional groups naturally present in or artificially introduced into said biological substance. Such functional groups are especially the functional groups $NH_2$, COOH, SH or OH. Such groups and the activation processes are described in detail by P. TIJSSEN in "Practice and Theory of Enzyme Immunoassays", Elsevier, 1985, said document being incorporated in the present description by way of reference.

Examples which may be mentioned in particular of functional groups appropriate for the purposes of the invention are amino, thio, cyano, isocyano, isothiocyano, thiocyano, carboxyl, hydroxyl, maleimido, succinimido, mercapto, phenol, imidazole, aldehyde, epoxide, halide, thionyl, sulfonyl, nitrobenzoyl, carbonyl, triazo, anhydride, halogenoacetate, hydrazino, acridine and other groups.

The particularly preferred groups are amino, thio and carboxyl groups, which have to be activated prior to covalent coupling with the biological substance, and maleimido, succinimido and isothiocyanate groups, which can bond directly with the biological substance.

The macrocyclic complexes of the invention are prepared by known processes.

The macrocyclic compounds are prepared by the techniques described in R. Ziessel et al., Helvetica Chimica Acta, 1990, 73, 1149, for macrocycles comprising bipyridine units. The other macrocycles can be prepared by the techniques described in the series of works entitled Supramolecular Chemistry, Springer Verlag Chemie, ed. F. Fögter. The base macrocyclic unit is then reacted with a halogenated derivative of the nitrogen-containing heterocyclic system in a polar aprotic solvent, the latter having been oxidized beforehand, especially by reaction with a peracid such as metachloroperbenzoic acid.

If it is desired to prepare a complex in which the radicals Ⓐ and/or Ⓑ consist of a nitrogen-containig heterocyclic system in which at least one of the nitrogen atoms carries an oxy group, the base macrocycle is prepared and is oxidized, preferably during its synthesis if it is in the form of a tosylated derivative, with a peracid such as metachloroperbenzoic acid. The tosylated macrocyclic compound is then deprotected and reacted with the halogenated derivative of the radicals Ⓒ and/or Ⓓ.

The preparation of the bipyridine macrocycle via a tosylated intermediate is described especially in J. Org. Chem., 1983, 48, 1848.

The macropolycyclic rare earth complexes according to the invention can be obtained by the conventional processes for the preparation of metal complexes, which consist in reacting the complexing compound with a donor compound of the cation to be complexed.

For example, the macropolycyclic complexes can be obtained by reacting a donor compound of the rare earth cation with the macropolycyclic compound having the characteristics defined above, each compound advantageously being in solution, preferably in the same solvent or in compatible solvents which are inert towards the complexation. In general, acetonitrile or methanol is used as the solvent and is heated to the reflux point.

According to another of its features, the invention relates to a method of reducing perturbations in a fluorescent assay using the above-described macrocyclic complexes as tracers, especially if the measuring medium is a biological medium and in particular a serum medium.

According to a final feature, the invention relates to the use of the above-described macrocyclic complexes for reducing the perturbations in the measuring medium of a fluorescent method of detecting and/or determining an analyte in a medium in which it may be present.

Said complexes have an important application in fluorescent immunoassays, in both the so-called competitive and excess assay methods, in the homogeneous or heterogeneous phase, which have been described in the prior art (Landon, Ann. Clin. Biochem., 1981, 18, 253, and E. SOINI et al., Clin. Chem., 1979, 25, 353).

In the present description:

"analyte" defines any substance or group of analogous substances to be detected and/or determined; and "receptor" defines any substance capable of binding specifically to a site on said analyte.

According to a preferred feature, the method of detecting and/or determining an analyte in which the macrocycles of the invention are used is a homogeneous method.

In particular, the macrocycles of the invention will be used in a fluorescent method of detecting and/or determining an analyte in a medium in which it may be present, said method consisting in:

1) adding to said medium a first reagent consisting of at least one receptor for said analyte, 2) adding a second reagent selected from the analyte or at least one of its receptors, one of the two reagents being coupled with a fluorescent compound to give consisting of a macrocyclic complex according to the invention, and the other reagent being coupled with a fluorescent acceptor compound, and it being possible for the order of addition of the reagents to be reversed, 3) incubating the resulting medium either after the addition of each reagent or after the addition of both reagents, 4) exciting the resulting medium at the excitation wavelength of the donor compound, and measuring, at equilibrium or under kinetic conditions, the signal emitted by the fluorescent acceptor compound.

Said complexes can also be used in a fluorescent method of detecting and/or determining an analyte in a medium in which it may be present, with the aid of an excess method consisting in:

2) adding, to said medium containing the target analyte, a first reagent consisting of at least one receptor for said analyte, coupled with a fluorescent donor compound consisting of a macrocyclic complex according to the invention, 2) adding a second reagent consisting of one or more other receptors for said analyte, said second reagent being coupled with a fluorescent acceptor compound, 3) incubating said medium after the addition of each reagent or after the addition of both reagents, 4) exciting the resulting medium at the excitation wavelength of the fluorescent donor compound by means of a light source, and 5) measuring the signal emitted by the fluorescent acceptor compound.

The above excess method will use in particular a single receptor for the analyte, which can be coupled either with the fluorescent donor compound or with the fluorescent acceptor compound.

According to an advantageous feature, the macrocyclic complexes according to the invention will be used in a fluorescent method of detecting and/or determining an analyte in a medium in which it may be present, with the aid of a competitive method consisting in:

1) adding, to said medium containing the target analyte, a first reagent consisting of a receptor for said analyte, coupled with a fluorescent donor compound consisting of a macrocyclic complex according to the invention, 2) adding a second reagent consisting of the analyte coupled with a fluorescent acceptor compound, 3) incubating said medium after the addition of each reagent or after the addition of both reagents, 4) exciting the resulting medium at the excitation wavelength of the fluorescent donor compound, and 5) measuring the signal emitted by the fluorescent acceptor compound.

In particular, the macrocyclic complexes described above will be used in a fluorescent method of detecting and/or determining an analyte in a medium in which it may be present, with the aid of a competitive method consisting in:

1) adding, to said medium containing the target analyte, a first reagent consisting of a receptor for said analyte, said receptor being coupled with a fluorescent acceptor compound, 2) adding, as a second reagent, the analyte being coupled with a fluorescent donor compound consisting of a macrocyclic complex according to the invention, 3) incubating said medium either after the addition of each reagent or after the addition of both reagents, 4) exciting the resulting medium at the excitation wavelength of the fluorescent donor compound, and 5) measuring the signal emitted by the fluorescent acceptor compound.

According to an advantageous feature, the first reagent and second reagent used in the above-indicated fluorescent methods of detecting and/or determining an analyte are added simultaneously to the medium containing the target analyte.

Preferably, the fluorescent donor compound used will be a macrocyclic complex in which the rare earth ion is europium, and the fluorescent acceptor compound used will be a compound selected from allophycocyanin, allophycocyanin B, phycocyanin C or phycocyanin R.

Another fluorescent donor compound which can be used is a macrocyclic terbium complex and another fluorescent acceptor compound which can be used is a compound selected from rhodamines, thionine, phycocyanin R, phycoerythrocyanin, phycoerythrin C, phycoerythrin B or phycoerythrin R.

The invention will be understood more clearly with the aid of the Examples below, which in no way imply a limitation.

Example 1

Preparation of the macrocyclic compound of formula (3):

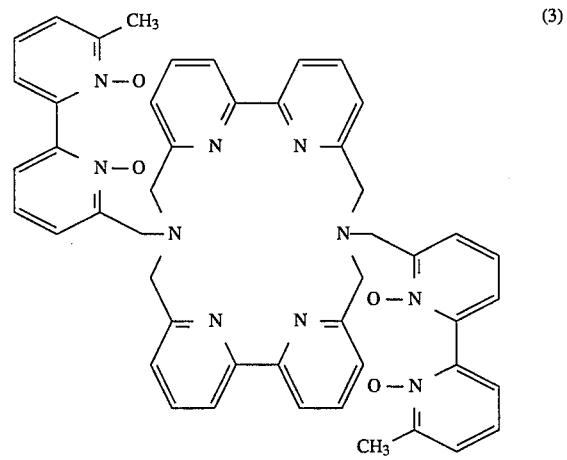

This compound is prepared according to the scheme below:

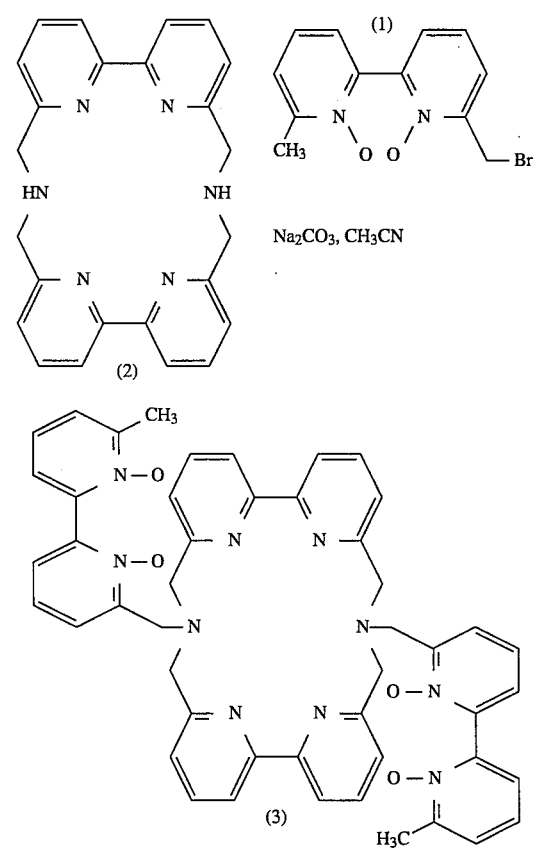

a) Preparation of compound (1)

A mixture of 6,6'-dimethyl-2,2'-bipyridine (2.76 g, 15 mmol) and N-bromosuccinimide (5.10 g, 28.6 mmol) is refluxed in 150 ml of chloroform for 30 min. 30 mg of benzoyl peroxide are then added. The mixture is subsequently refluxed for 2 h and then filtered to separate off the succinimide.

The solution is cooled to 0° C. and the solid which deposits is filtered off and washed with methanol. 1.65 g of 6,6'-bis(bromomethyl)-2,2'-bipyridine are recovered in the form of a white solid crystal. The filtrate obtained above from the chloroform solution is concentrated and chromatographed on a silica column (eluent: $CH_2Cl_2$/MeOH 98:2).

This gives 1.38 g of 6,6'-bis(bromomethyl)-2,2'-bipyridine, 0.55 g of 6-methyl-6'-bromomethyl-2,2'-bipyridine (melting point: 88° C.) and 0.9 g of 6,6'-bis(dibromomethyl)-2,2'-bipyridine.

0.5 g (1.9 mmol) of 6-methyl-6'-bromomethyl-2,2'-bipyridine is solubilized in 100 ml of chloroform which has first been passed over alumina (Basic-activity activity I, Merck, U.S.A.). A solution of 1.2 g of metachloroperbenzoic acid (55% $H_2O$) in 50 ml of chloroform, i.e. 2 equivalents of acid per equivalent of brominated derivative, is added dropwise. After 4 h, a further 2 equivalents of metachloroperbenzoic acid are added dropwise. After stirring overnight at room temperature, the mixture is evaporated to dryness and dried under a vane pump vacuum. The residue is washed 5 times with ether to give 400 mg of the expected product in the form of a pale yellow powder (yield: 71%). Melting point: 125° C.

b) Preparation of compound (3)

A solution of 1.1 g (3.70 mmol) of compound (1) in 200 ml of $CH_3CN$ is added dropwise to a mixture containing 0.45 g (1.14 mmol) of compound (2) (bipyridine macrocycle described in J. Org. Chem., 1983, 48., 4848) and 3 g (17 mmol) of $Na_2CO_3$ in 300 ml of freshly distilled MeCN under reflux and under a nitrogen atmosphere, with stirring.

Reflux is maintained for 24 h, with stirring. The mixture is filtered hot and the filtrate is concentrated under vacuum at room temperature. The crude product is dissolved in $CHCl_3$ (200 ml), washed 3 times with water, dried over $MgSO_4$ and evaporated. After chromatography on alumina (eluent: $CH_2C_2$/MeOH 9:1), 400 mg of the expected product are obtained in the form of a white powder (yield: 42%). Melting point: 235° C. (decomposition).

$^1$H NMR spectrum ($CDCl_3$): 2.59 (2CH3); 4.21 (4CH$_2$); 4.55 (2CH$_2$); 7.09 (d, J=7.3, 4H); 7.31–7.47 (m, 14H); 7.74 (d, J=7.5, 4H); 8.22–8.27 (m, 2H). $^{13}$C NMR spectrum ($CD_3OD$): 18.1 (2CH$_3$); 58.2 (2CH$_2$); 62.0 (4CH$_2$); 121.2; 124.9; 25.5; 127.7; 128.1; 128.5; 130.8; 139.3; (24H); 145.3; 145.4; 148.8; 150.4; 156.0; 159.9: (16C). Elemental analysis: calculated for $C_{48}H_{44}O_5N_{10}.H_2O$ (840.91) C:68.55; H:5.27; N:16.66 found C:68.34; H:5.09; N:16.38

EXAMPLE 2

Preparation of a macrocyclic europium complex (macrocycle: compound (3) of Example 1)

17 mg of $EuCl_3.6H_2O$ (4.6.10$^{-5}$ mol) are added, with stirring, to a solution of 37 mg of compound (3) (4.5.10$^{-5}$ mol) in 15 ml of methanol at room temperature. Stirring is maintained for 48 h under a nitrogen atmosphere. 30 ml of $Et_2O$ are then added, causing the appearance of a white precipitate, which is isolated by centrifugation. 50 mg (99%) of the expected product are thus recovered in the form of a white powder. Melting point: 190° C. (decomposition).

FAB mass spectrum (NBA): 1045.0 ([M+Eu+2Cl]$^+$); 1010.1 ([M+Eu+Cl]$^+$); 994.1 ([M–O+Eu+Cl]$^+$). Elemental analysis: calculated for $C_{48}H_{42}O_4N_{10}.EuCl_3.6H_2O$ (1189.30) C:48.47; H:4.57; N:11.78 found C:48.71; H:4.94; N:10.89

Example 3

Preparation of a macrocyclic terbium complex (macrocycle: compound (3) of Example 1)

12 g of $TbCl_3.6H_2O$ (3.2.10$^{-5}$ mol) are added, with stirring, to a solution of 25 mg of compound (3) (3.04.10$^{-5}$ mol) in 15 ml of methanol at room temperature. Stirring is maintained for 48 h under a nitrogen atmosphere. 30 ml of $Et_2O$ are then added, causing the appearance of a white precipitate, which is isolated by centrifugation. 33 mg (94%) of the expected product are thus recovered in the form of a yellow powder. Melting point: 190° C. (decomposition).

FAB mass spectrum (NRA): 1050.9 ([M+Tb+2Cl$^-$]$^+$); 1014.9 ([M+Tb+Cl]$^+$). Elemental analysis: calculated for $C_{48}H_{42}O_4N_{10}.TbCl_3.H_2O$ (1106.19) C:52.11; H:4.01; N:12.66 found C:51.83; H:4.22; N:12.28

Example 4

Preparation of the macrocyclic compounds of formulae (5) and (6)

These compounds are prepared from compound (2) of Example 1 according to the scheme below.

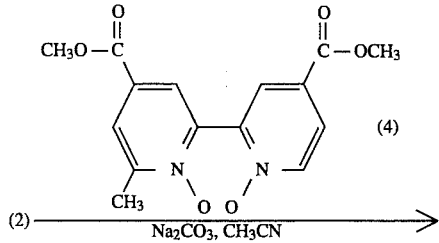

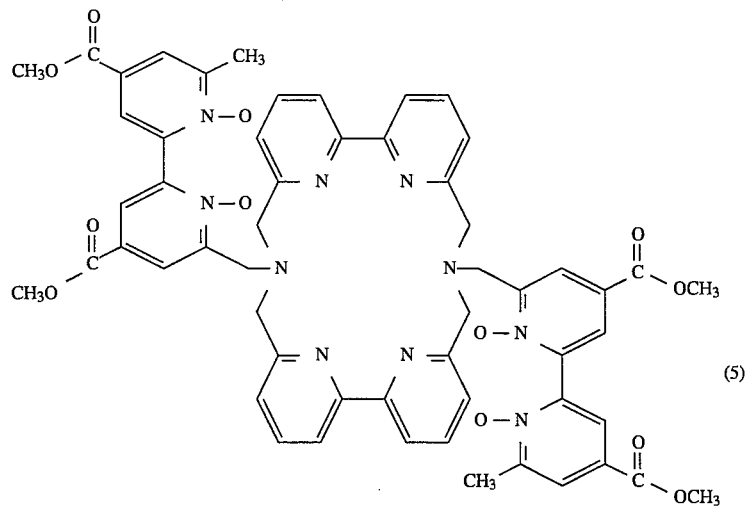

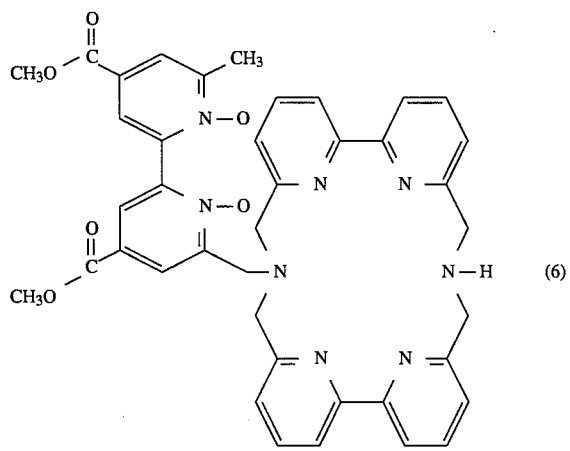

a. Preparation of compound (4)

A mixture of dimethyl 6,6'-dimethyl-2,2'-bipiridine-4,4'-dicarboxylate (4.4 g) and N-bromosuccinimide (9.76 g) is refluxed for 30 min in 240 ml of carbon tetrachloride.

0.54 g of 2,2'-azobis(2-methylpropionitrile) is then added. The mixture is refluxed for 4 h.

The solution is then filtered hot and cooled for 12 h at 4° C.

The filtrate obtained is evaporated and chromatographed on a silica column (eluent: $CH_2Cl_2$/hexane 50/50).

This gives 2.06 g of dimethyl 6-methyl-6'-bromomethyl-2,2'-bipyridine-4,4'-dicarboxylate.

2.06 g (5.4 mmol) of dimethyl 6-methyl-6'-bromomethyl-2,2'-bipyridine-4,4'-dicarboxylate are solubilized in 200 ml of chloroform. A solution of 3.35 g (0.1 mM) of metachloroperbenzoic acid in 40 ml of chloroform is added dropwise. After 12 h, a chloroform solution containing 6.7 g of metachloroperbenzoic acid is added dropwise.

After 24 h, the mixture is evaporated to dryness and the residue is dried under a vane pump vacuum. It is washed 4 times with 50 ml of ethyl ether and purified on silica (eluent: $CHCl_3$/cyclohexane 90/10) to give 1.05 g of the expected product (yield: 47%).

b. Preparation of compounds (5) and (6)

A mixture containing 48 mg (0.12 mM) of compound (2) and 0.13 g (1.2 mM) of $Na_2CO_3$ is refluxed for 30 min in 150 ml of $CH_3CN$.

A mixture containing 100 mg (0.24 mM) of compound (1) dissolved in 50 ml of $CH_3CN$ is then added dropwise.

The mixture is stirred under reflux for 24 h and filtered hot and the filtrate is concentrated under vacuum.

EXAMPLE 5

Preparation of macrocyclic europium complexes in which the macrocycles are compounds (5) and (6) of Example 4

302 mg of $EuCl_3.6H_2O$ (0.82 mM) in 60 ml of anhydrous methanol are added to the crude product obtained in Example 4. The mixture is refluxed for 2h.

The solution is then cooled and evaporated. The crude reaction product is then purified on a reversed-phase column in $CH_3CN/H_2O$/TFA.

This gives the following:

18 mg of macrocyclic complex (6)—FAB mass spectrum (NBA):

1101 [$M+Eu+2CF_3COO^-$]

988 [$M+Eu+CF_3COO^-$]

29 mg of macrocyclic complex (5)—FAB mass spectrum (NBA):

1431 [$M+Eu+2CF_3COO^-$]

EXAMPLE 6

Preparation of a macrocyclic compound of formula (7)

This compound is prepared from compounds (1) and (2) of Example 1 and compound (4) of Example 4 according to the scheme below.

EXAMPLE 7

Preparation of a macrocyclic europium complex in which the macrocycle is compound (7) of Example 6

This complex is prepared as described above in Example 5.

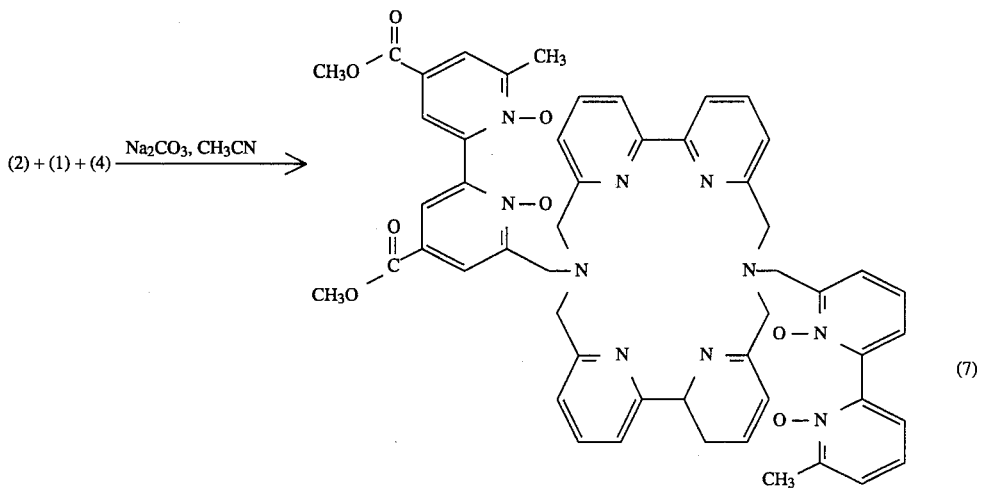

A solution of 0.55 g (1.8 mM) of compound (1) in 100 ml of $CH_3CN$ is added dropwise, under reflux, to a mixture of 0.45 g (1.14 mM) of compound (2) and 3 g (17 mM) of $Na_2CO_3$ in 150 ml of $CH_3CN$ and 125 ml of $CH_2Cl_2$.

The mixture is stirred under reflux for 12 h, filtered hot and concentrated under vacuum. The crude product is purified on an alumina column to give 207 mg of the monosubstituted product.

A solution of 0.1 g of compound (4) (0.24 mM) in 20 ml of $CH_3CN$ is added dropwise, under reflux, to a mixture of 0.20 g of the monosubstituted product (0.23 mM) and 0.6 g (3.4 mM) of $Na_2CO_3$ in 60 ml of $CH_3CN$.

The solution is stirred under reflux for 24 h. The mixture is filtered hot and concentrated under vacuum. The product is washed with water.

This gives 57 mg of compound (7) (0.05 mM).

FAB mass spectrum (NBA):

1161 [M+Eu+2Cl]

1126 [M+Eu+Cl]

EXAMPLE 8

Preparation of a macrocyclic europium complex in which the macrocycle is the compound of formula (8)

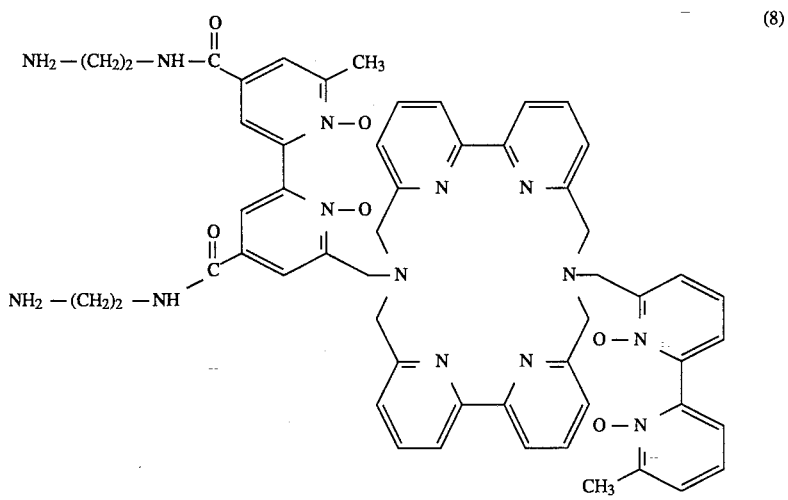

This compound is obtained from the macrocycle of Example 7 with the aid of an aminolysis reaction such as that described in the patent EP 0 321 353 (see especially Example 3, step B). Briefly, the macrocycle is subjected to aminolysis by being added in portions to 4 ml of ethylenediamine which has been distilled over KOH and preheated to 90° C. The reaction mixture obtained is stirred for a further 1 h and then cooled to room temperature. The excess ethylenediamine is then removed under vacuum to give an oil. This is taken up with 2 ml of a toluene/CH₃OH mixture (2/1), which in turn is removed under vacuum to give a beige powder. 1.8 $NH_2$ per mol of chelate are determined by colorimetry.

EXAMPLE 9

Demonstration of the stability and the name-sensitivity or quenching of the macrocyclic europium complexes of Examples 2, 5, 7 and 8

The determinations below were made with a PERKIN-ELMER LS 5 spectrometer.

The lifetime of the complexes tested was measured in the following manner: the emission spectrum of the peak situated between 600 and 650 nm was recorded, the solution being excited in one of the absorption peaks. The "phosphorescence" mode was used and the value of the window was set at 1 ms=tg. The recordings were made for several values of $t_d$ (delay), namely 0.1, 0.2, 0.3, 0.4 and 0.5 ms. The peak intensity $I_t$ was measured and τ was determined by the formula $$I_t = I_o\, e^{t/\tau}$$

$$\tau = \frac{0.434\, t}{\log I_o - \log I_t}$$

The compounds were tested in water and in a 100 mM phosphate buffer of pH 7.2 at a complex concentration of about $10^{-6}$ M/l.

The complexes containing the macrocyclic compounds below were tested in comparison with the europium complexes of Examples 2, 5, 7 and 8.

Compound A:

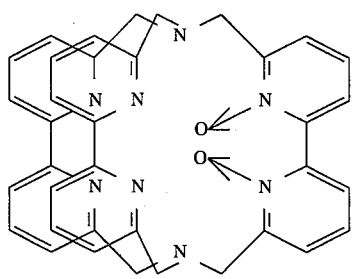

Compound B:

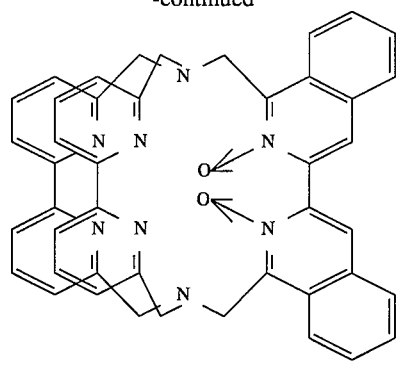

Compound C:

Compound D:

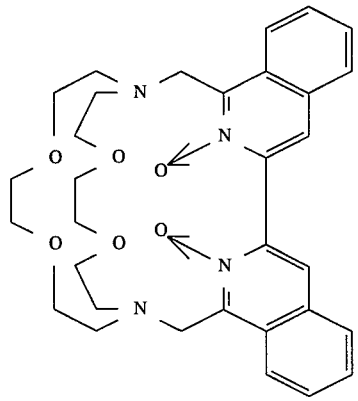

Compound E:

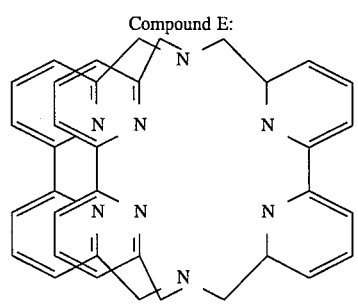

The preparation of compounds A and B is described in J. M. Lehn et al., Helvetica Chimica Acta, 1991, 74, 572, that of compound C is described in R. Ziessel et al., Helvetica Chimica Acta, 1990, 73, 1149, that of compound D is described in J. M. Lehn et al., Helvetica Chimica Acta, 1990, 73, 106, and that of compound E is described in the patent EP 0 180 492.

The results are given in Table 1 below.

The measurements in serum were made in human serum diluted to 1/3 with 100 mM phosphate buffer of pH 7.2.

The lifetimes (τ) are expressed in ms.

TABLE 1

| Complex tested | τ in H$_2$O | τ in PO$_4$ buffer | τ in serum | Stability in PO$_4$ buffer | Quenching in serum | |
|---|---|---|---|---|---|---|
| | | | | | $\left(1 - \dfrac{\tau\,\text{serum}}{\tau\,\text{PO}_4}\right)\%$ | $\left(1 - \dfrac{\tau\,\text{serum}}{\tau\,\text{H}_2\text{O}}\right)\%$ |
| Example 2 macrocycle (3) | 0.48 | 0.66 | 0.62 | stable | 6% | exaltation + 30% |
| Example 5 macrocycle (5) | 0.15 | — | 0.19 | stable | — | exaltation + 27% |
| Example 5 macrocycle (6) | 0.17 | — | 0.19 | stable | — | exaltation + 12% |
| Example 7 macrocycle (7) | 0.38 | — | 0.44 | stable | — | exaltation + 16% |
| Example 8 macrocycle (8) | 0.38 | 0.44 | 0.53 | stable | exaltation + 20% | exaltation + 39% |
| A | 0.46 | 0.84 | 0.2 | stable | 75% | 56% |
| B | 0.39 | 0.49 | 0.14 | stable | 71% | 64% |
| C | 1.5 | 1.2 | 0.7 modification of the emission spectrum | loss of half the signal in 1 h 30 min and formation of a precipitate | 40% modification of the emission spectrum | 53% |
| D | 0.38 | 0.63 | 0.2 | stable | 68% | — |
| E | 0.34 | 0.52 | 0.15 | stable | 71% | 47% |

The results show that although most of the compounds tested are stable in phosphate buffer (stability evaluated by the permanence of the peak height), only the complexes according to the invention are significantly insensitive to the quenching phenomenon or even exhibit exaltation of the fluorescence in serum, relative to the fluorescence emitted in water.

What is claimed is:

1. A macrocyclic rare earth complex which consists of at least one rare earth salt complexed by a macrocyclic compound of formula (I):

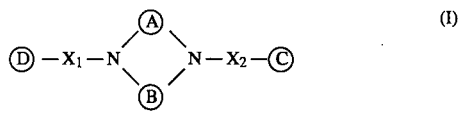

in which:

The bivalent radicals Ⓐ, Ⓑ, Ⓒ, and Ⓓ, which are identical or different, are hydrocarbon chains optionally containing one or more heteroatoms, at least one of said radicals containing at least one molecular unit or essentially consisting of a molecular unit possessing a triplet energy greater than the energy of the emission level of the complexed rare earth ion, at least one of said radicals consisting of a substituted or unsubstituted nitrogen-containing heterocyclic system in which at least one of the nitrogen atoms carries an oxy group, and it being possible for one of the radicals Ⓒ or Ⓓ not to exist; and $X_1$ and $X_2$, which are identical or different, are either hydrogen, in which case one or both radicals Ⓒ, and Ⓓ do not exist, or a hydrocarbon chain $(CH_2)_n$ optionally interrupted by 1 or more heteroatoms, n being an integer from 1 to 10, with the proviso that if the radicals Ⓐ, and/or Ⓑ are a nitrogen-containing heterocyclic system in which at least one of the nitrogen atoms carries an oxy group, the radicals Ⓒ and/or Ⓓ are selected from the group consisting of biquinolines, biisoquinolines, bipyridines, terpyridines, coumarins, bipyrazines, bipyrimidines and pyridines.

2. A complex according to claim 1 wherein at least one of the bivalent radicals Ⓐ and Ⓑ contains at least one molecular unit or essentially consists of a molecular unit possessing a triplet energy greater than the energy of the emission level of the complexed rare earth ion, and at least one of the radicals Ⓒ and Ⓓ consists of a nitrogen-containing heterocyclic system in which at least one of the nitrogen atoms carries an oxy group.

3. A complex according to claim 1 wherein the radicals Ⓐ and Ⓑ are identical.

4. A complex according to claim 1 wherein the radicals Ⓒ and Ⓓ are identical.

5. A complex according to claim 1 wherein $X_1$ and $X_2$ are identical.

6. A complex according to claim 1 wherein the triplet energy of the molecular unit is greater than 17,300 cm$^{-1}$.

7. A complex according to claim 1 wherein the molecular unit is selected from the group consisting of phenanthroline, anthracene, bipyridines, biquinolines, terpyridines, coumarins, bipyrazines, bipyrimidines, azobenzene, azopyridine, pyridines or 2,2'-bisisoquinoline, or the units

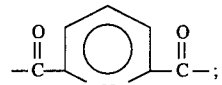

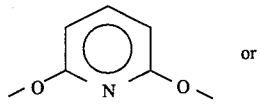

or

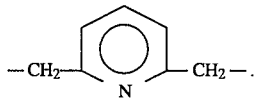

8. A complex according to claim 1 wherein the nitrogen-containing heterocyclic system is selected from the following units: pyridine N-oxide, bipyridine N-oxide, bipyridine di-N-oxide, bisisoquinoline N-oxide and bisisoquinoline di-N-oxide.

9. A complex according to claim 1 wherein the molecular unit possessing a triplet energy greater than the energy of the emission level of the complexed rare earth ion, and the nitrogen-containing heterocyclic system in which at least one of the nitrogen atoms carries an oxy group, are one and the same unit.

10. A complex according to claim 1 wherein the rare earth ion is selected from europium, terbium, samarium and dysprosium.

11. A complex according to claim 1 wherein at least one of the radicals Ⓐ, Ⓑ, Ⓒ and Ⓓ is substituted by a group —CO—NH—Y—Z, in which:

Y is a spacer arm or group which consists of a bivalent organic radical selected from linear or branched $C_1$ to $C_{20}$ alkylene groups optionally containing one or more double bonds and/or optionally interrupted by one or more heteroatoms such as oxygen, nitrogen, sulfur or phosphorus, from $C_5$–$C_8$ cycloalkylene groups or from $C_6$–$C_{14}$ arylene groups, said alkylene, cycloalkylene or arylene groups optionally being substituted by alkyl, aryl or sulfonate group; and Z is a functional group capable of bonding covalently with a biological substance.

12. A complex according to claim 1 wherein the macrocyclic compound is the compound of the formula

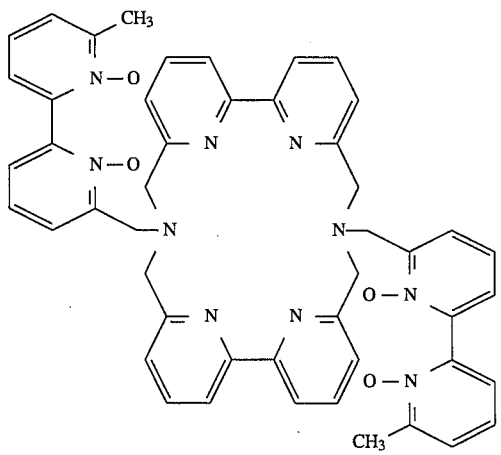

13. A method of reducing perturbations in a fluorescent assay of an analyte, said method comprising the steps of:

(a) providing a macrocyclic compound having the formula (I):

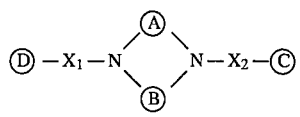

in which:

The bivalent radicals Ⓐ, Ⓑ, Ⓒ, and Ⓓ, which are identical or different, are hydrocarbon chains optionally containing one or more heteroatoms, at least one of said radicals containing at least one molecular unit or essentially consisting of a molecular unit possessing a triplet energy greater than the energy of the emission level of the complexed rare earth ion, at least one of said radicals consisting of a substituted or unsubstituted nitrogen-containing heterocyclic system in which at least one of the nitrogen atoms carries an oxy group, and it being possible for one of the radicals Ⓒ or or Ⓓ not to exist; and $X_1$ and $X_2$, which are identical or different, are either hydrogen, in which case one or both radicals Ⓒ, and Ⓓ do not exist, or a hydrocarbon chain $(CH_2)_n$ optionally interrupted by 1 or more heteroatoms, n being an integer from 1 to 10, with the proviso that if the radicals Ⓐ, and/or Ⓑ are a nitrogen-containing heterocyclic system in which at least one of the nitrogen atoms carries an oxy group, the radicals Ⓒ and/or Ⓓ are selected from the group consisting of biquinolines, biisoquinolines, bipyridines, terpyridines, coumarins, bipyrazines, bipyrimidines and pyridines;

(b) adding said macrocyclic compound as a tracer to a measuring medium for a fluorescent assay.

14. A method according to claim 13 wherein the measuring medium is a biological medium.

15. A method according to claim 14 wherein the measuring medium is a serum medium.

16. A method for reducing perturbations in the measuring medium of a fluorescent assay method, said method comprising the steps of:

(a) providing a macrocyclic compound having the formula (I):

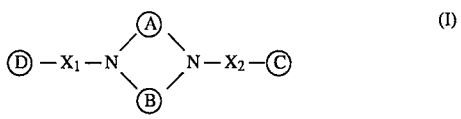

in which:

The bivalent radicals Ⓐ, Ⓑ, Ⓒ, and Ⓓ, which are identical or different, are hydrocarbon chains optionally containing one or more heteroatoms, at least one of said radicals containing at least one molecular unit or essentially consisting of a molecular unit possessing a triplet energy greater than the energy of the emission level of the complexed rare earth ion, at least one of said radicals consisting of a substituted or unsubstituted nitrogen-containing heterocyclic system in which at least one of the nitrogen atoms carriers an oxy group, and it being possible for one of the radicals Ⓒ or Ⓓ not to exist; and $X_1$ and $X_2$, which are identical or different, are either hydrogen, in which case one or both radicals Ⓒ, and Ⓓ do not exist, or a hydrocarbon chain $(CH_2)_n$ optionally interrupted by 1 or more heteroatoms, n being an integer from 1 to 10, with the proviso that if the radicals Ⓐ, and/or Ⓑ are a nitrogen-containing heterocyclic system in which at least one of the nitrogen atoms carries an oxy group, the radicals Ⓒ and/or Ⓓ are selected from the group consisting of biquinolines, biisoquinolines, bipyridines, terpyridines, coumarins, bipyrazines, bipyrimidines and pyridines;

(b) adding said macrocyclic compound to a measuring medium for a fluorescent assay method for detecting and/or determining the presence of an analyte, said macrocyclic compound thereby reducing the perturbations in the measuring medium.

17. A method according to claim 16 wherein said fluorescent assay method is a homogeneous method.

18. A method according to claim 16 for detecting and/or determining an analyte in a medium in which it can be present, said method including the steps of:

1) adding to said medium a first reagent consisting of at least one receptor for said analyte, 2) adding a second reagent selected from the analyte or at least one of its receptors, one of the two reagents being coupled with a fluorescent donor compound consisting of said macrocyclic compound having the formula (I), and the outer reagent being coupled with a fluorescent acceptor compound, and it being possible for the order of addition of the reagents to be reversed, 3) incubating the resulting medium either after the addition of each reagent or after the addition of both reagents, 4) exciting the resulting medium at the excitation wavelength of the donor compound, and 5) measuring, at equilibrium or under kinetic conditions, the signal emitted by the fluorescent acceptor compound.

19. A method according to claim 16 for detecting and/or determining an analyte in a medium in which it can be present, with the aid of an excess method including the steps of:

1) adding, to said medium containing the target analyte, a first reagent consisting of at least one receptor for said analyte, coupled with a fluorescent donor compound consisting of said macrocyclic compound having the formula (I), 2) adding a second reagent consisting of one or more other receptors for said analyte, said second reagent being coupled with a fluorescent acceptor compound, 3) incubating said medium after the addition of each reagent or after the addition of both reagents, 4) exciting the resulting medium at the excitation wavelength of the fluorescent donor compound by means of a light source, and 5) measuring the signal emitted by the fluorescent acceptor compound.

20. A method according to claim 16 for detecting and/or determining an analyte in a medium in which it can be present, with the aid of a competitive method including the steps of:

1) adding, to said medium containing the target analyte, a first reagent consisting of a receptor for said analyte, coupled with a fluorescent donor compound consisting of said macrocyclic compound having formula (I), 2) adding a second reagent consisting of the analyte coupled with a fluorescent acceptor compound, 3) incubating said medium after the addition of each reagent or after the addition of both reagents, 4) exciting the resulting medium at the excitation wavelength of the fluorescent donor compound, and 5) measuring the signal emitted by the fluorescent acceptor compound.

21. A method according to claim 16 for detecting and/or determining in analyte in a medium in which it can be present, with the aid of a competitive method including the steps of:

1) adding, to said medium containing the target analyte, a fist reagent consisting of a receptor for said analyte, said receptor being coupled with a fluorescent acceptor compound, 2) adding, as a second reagent, the analyte being coupled with a fluorescent donor compound consisting of said macrocyclic compound having the formula (I), 3) incubating said medium either after the addition of each reagent or after the addition of both reagents, 4) exciting the resulting medium at the excitation wavelength of the fluorescent donor compound, and 5) measuring the signal emitted by the fluorescent acceptor compound.

22. A method according to claim 18 wherein the first reagent and second reagent are added simultaneously to the medium containing the target analyte.

23. A method according to claim 18 wherein a single receptor for the analyte is used which is coupled either with the fluorescent donor compound or with the fluorescent acceptor compounds.

24. A method according to claim 18 wherein the rare earth ion of the macrocyclic complex used as the fluorescent donor compound is europium, and wherein the fluorescent acceptor compound is selected from the group consisting of allophycocyanin, allophycocyanin B, phycocyanin C or phycocyanin R.

25. A method according to claim 18 wherein the rare earth ion of the macrocyclic complex used as the fluorescent donor compound is terbium, and wherein the fluorescent acceptor compound is selected from the group consisting of rhodamines, thionine, phycocyanin R, phycoerythrocyanin, phycoerythrin C, phycoerythrin B or phycoerythrin R.

* * * * *

UNITED STATES PATENT AND TRADEMARK OFFICE
CERTIFICATE OF CORRECTION

PATENT : 5,457,184
DATED : October 10, 1995
INVENTOR(S) : Jean-Marie Lehn et al.

It is certified that error appears in the above-identified patent and that said Letters Patent is hereby corrected as shown below:

In the specification:

Column 16, line 16, insert the chemical structure of "Compound C".

- Compound C:

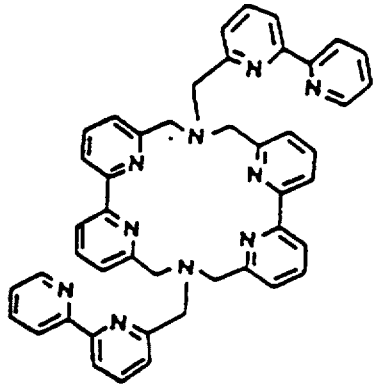

Signed and Sealed this

First Day of October, 1996

Attest:

BRUCE LEHMAN

Attesting Officer

Commissioner of Patents and Trademarks